United States Patent [19]
Poole, Jr.

[11] Patent Number: 5,181,508
[45] Date of Patent: * Jan. 26, 1993

[54] MOLDED CONNECTOR

[76] Inventor: Samuel E. Poole, Jr., 6354 Saint Andrews Cir., Fort Myers, Fla. 33919

[*] Notice: The portion of the term of this patent subsequent to Sep. 4, 2007 has been disclaimed.

[21] Appl. No.: 562,754

[22] Filed: Aug. 6, 1990

Related U.S. Application Data

[63] Continuation-in-part of Ser. No. 301,723, Jan. 26, 1989, Pat. No. 4,953,547.

[51] Int. Cl.$^5$ .............................................. A61M 16/10
[52] U.S. Cl. ........................... 128/203.12; 128/207.14; 128/912
[58] Field of Search ................... 128/207.14, 207.15, 128/200.26, 203.12, 202.27, 911, 912, 207.16, DIG. 26

[56] References Cited

U.S. PATENT DOCUMENTS

| | | | |
|---|---|---|---|
| 374,831 | 12/1887 | Harrington | 128/207.12 |
| 3,630,196 | 12/1971 | Bird | 128/200.18 |
| 3,731,691 | 5/1973 | Chen | 604/100 |
| 4,327,721 | 5/1982 | Goldin et al. | 128/207.15 |
| 4,601,701 | 7/1986 | Mueller, Jr. | 604/83 |
| 4,622,968 | 11/1986 | Persson | 128/200.26 |
| 4,669,463 | 6/1987 | McConnell | 128/207.14 |
| 4,805,611 | 2/1989 | Hodgkins | 128/207.14 |
| 4,852,583 | 8/1989 | Walker | 128/719 |

Primary Examiner—David A. Wiecking
Assistant Examiner—Stephen R. Funk
Attorney, Agent, or Firm—Dominik, Stein, Saccocio, Reese, Colitz & Van Der Wall

[57] ABSTRACT

An improved drug administering endotracheal respiration system for administering vital life-saving drugs into the lungs of a victim while maintaining the flow of life-supporting gas thereto via ventilation apparatus comprising in combination a gas supply; a tube for establishing gas flow exchange between the lungs of the victim and the gas supply, the tube having a proximal end and a distal end for insertion into the trachea of the victim; and a connector for coupling the proximal end of the tube to the gas supply, the connector being formed as a cylinder with a gas input end and a gas discharge end and a linear axial passageway therebetween, the connector having a hypodermic needle port adapted for receiving a hypodermic needle for injecting vital life-saving drugs in liquid form into the passageway and then into the distal end of the tube intermixed with the gas, the hypodermic needle port having a portion integrally formed with the connector and a portion separable therefrom, the connector further having a syringe port adapted for receiving a syringe for injecting vital life-saving drugs in liquid form into the passageway and then into the distal end of the tube intermixed with the gas, the syringe port having a portion integrally formed with the connector and a portion separable therefrom, the main axial passageway adapted for atomizing and intermixing of the flow of life-saving drugs with the life-supporting gas.

10 Claims, 4 Drawing Sheets

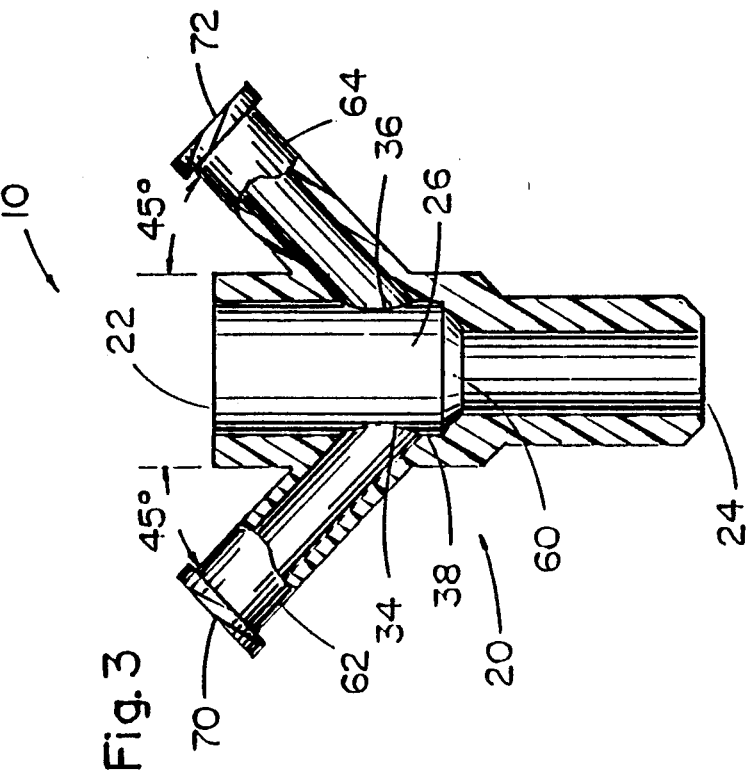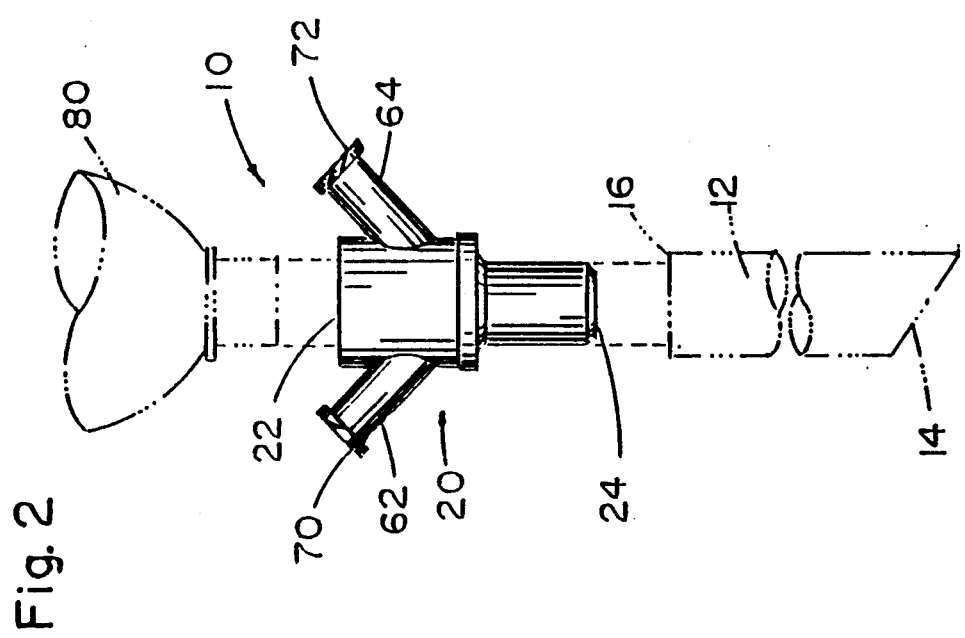

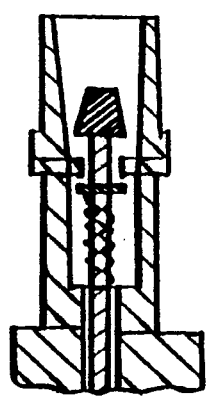
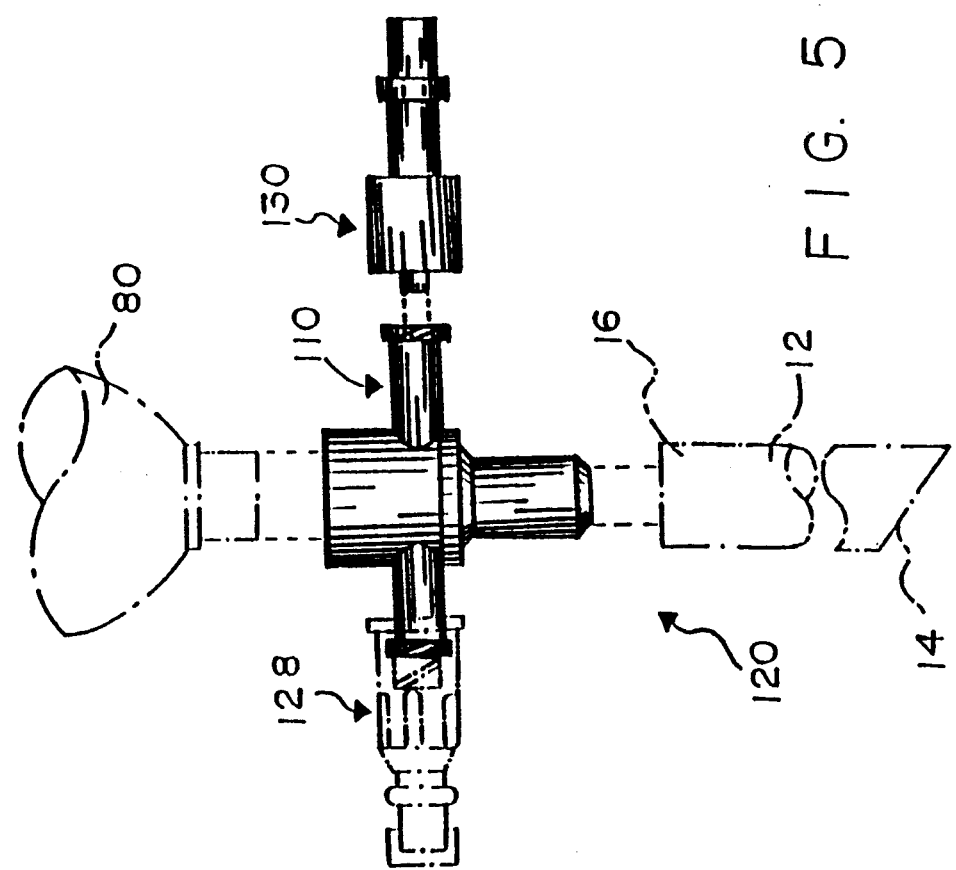
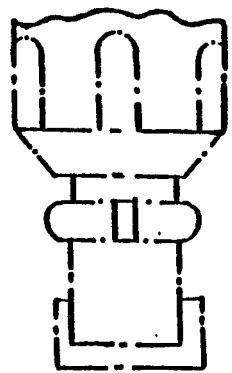

MOLDED CONNECTOR

BACKGROUND OF THE INVENTION

Related Application

This application is a continuation-in-part of U.S. patent application Ser. No. 07/301,723 filed Jan. 26, 1989 now U.S. Pat. No. 4,953,547.

SUMMARY OF THE INVENTION

This invention relates to improved drug administering endotracheal respiration systems, and more particularly, to devices used by paramedics, nurses, doctors, etc. to administer drugs for coupling endotracheal tubes to supplies of gas such as air or oxygen and for allowing the introduction of medicine while maintaining such supply of gas.

Description of The Background Art

Conventional systems for tracheal intubation are employed routinely by health care professionals in hospital settings. The function of tracheal intubation is to provide mechanical assistance to patients for their secure airway and respiration functions. Such mechanical assistance is effected by an endotracheal tube extending from a patient's lungs to exterior of the patient where it is coupled to a ventilation source for the administration of oxygen, air or other gasses. In hospital settings, where environmental conditions are excellent, intravenous injections are performed routinely for the most rapid administration of life-saving drugs even when a patient is being assisted by an endotracheal tube.

In pre-hospital settings, endotracheal tubes are also employed by paramedics or the like. Generally, the patient is a victim of an accident or another life-threatening medical emergency event that requires the assistance of a mechanical respiration apparatus to supplement an abnormal respiration function. As in hospital settings, the preferred method of injecting life-saving drugs in emergency life-threatening situations is intravenous. Unfortunately, the use of intravenous injection of life-saving drugs in a pre-hospital setting is not always secured by I-V therapy. Hence, the alternative of intratracheal drug administration in life-threatening situations is gaining acceptance.

Current endotracheal respiration systems allow for intratracheal drug injections only after disconnecting the life-supporting ventilation apparatus supplied with air, oxygen, or other life-supporting fluid. There is thus a need for an endotracheal respiration system that allows for the introduction of life-saving drugs while continuing the flow of life-supporting gasses.

Hospitals and providers of pre-hospital medicine are increasingly utilizing sterile instruments on a use-once, throw-away basis. This trend is due to the desire to reduce the transmission of hospital infection from one patient to another. Endotracheal respiration systems are in the use-once, throw-away category. The conventional endotracheal respiration system usually comprises at least two separate parts, the tube and a connector for coupling to a ventilation apparatus. The parts are manufactured individually and then assembled, tested and finally packaged in a sterile container. Accordingly, the materials and labor costs for an endotracheal respiration system that is used only once are relatively high.

The need thus exists for an endotracheal respiration system that is inexpensive, convenient and allows for the introduction of life-saving drugs without interrupting the flow of life-supporting gasses and that can easily be manufactured with few parts, assembled, tested and packaged in a sterile container for use in hospitals and pre-hospital settings on a use-once, throw-away basis.

Various approaches are disclosed in the literature to improve endotracheal respiration systems, including drug administering and non-drug administering endotracheal systems. By way of example, note U.S. Pat. Nos. 4,739,756 issued to Horn, 4,669,463 to McConnell and 4,622,968 to Persson, all of which disclose endotracheal respiration systems with a syringe medication injection port. U.S. Pat. No. 4,681,100 to Brychta discloses two ports. The patent to Horn also discloses longitudinal bores located in the walls of the endotracheal tube to transport the medication to an ejection ring attached to the distal end of the tube.

U.S. Pat. No. 3,616,799 issued to Sparks discloses an improved sail cuff for an endotracheal tube, while U.S. Pat. No. 4,751,924 issued to Hammerschmidt et al discloses a second balloon located on the proximal end of the endotracheal tube to signal when the first balloon or cuff located on the distal end of the endotracheal tube is properly pressurized.

Ellachar, in U.S. Pat. No. 4,700,700 discloses an inflatable cuff located on the endotracheal tube to avoid long term physical damage to the larynx, and U.S. Pat. No. 4,722,335 issued to Vilasi discloses a double wall segmented endotracheal tube that seals itself against the wall of the trachea without the need for an inflatable cuff.

Although many such advances are noteworthy to one extent or another, none achieves the objects of an efficient, reliable, inexpensive, convenient to use readily manufactured drug administering endotracheal respiration system designed to accommodate the needs of a wide variety of life threatening emergency situations in various settings.

As illustrated by the great number of prior patents and known endotracheal respiration systems and drug administering techniques, efforts are continuously being made in an attempt to allow simultaneous medication injection of life-saving drugs without interrupting the flow of life supporting gasses. The printed publication Journal of Prehospital Medicine, Volume 2, #1, July—September, 1988, page 1, appears to disclose an endotracheal respiration system with multiple medication injection capability through a single, common medication injection port. The device, however, appears to have more parts than the present invention and also appears to allow direct intratracheal drug administration without sufficient diffusion in the gas stream of the life-supporting gasses.

None of these previous efforts, however, provides the benefits attendant with the present invention. Additionally, prior techniques do not suggest the present inventive combination of component elements as disclosed and claimed herein. The present invention achieves its intended purposes, objectives and advantages over the prior art devices through a new, useful and unobvious combination of component elements, which is simple to use, with the utilization of a minimum number of functioning parts, at a reasonable cost to manufacture, assemble and test, and by employing only readily available materials.

Therefore, the object of the present invention is to provide an improved drug administering endotracheal respiration system for administering vital life-saving drugs into the lungs of a victim while maintaining the flow of life-supporting gas thereto via ventilation apparatus comprising in combination a gas supply; a tube for establishing gas flow exchange between the lungs of the victim and the gas supply, the tube having a proximal end and a distal end for insertion into the trachea of the victim; and a connector for coupling the proximal end of the tube to the gas supply, the connector being formed as a cylinder with a gas input end and a gas discharge end and a linear axial passageway therebetween, the connector having a first port adapted for injecting vital life-saving drugs in liquid form into the passageway and then into the distal end of the tube intermixed with the gas, the first port having a portion integrally formed with the connector and a portion separable therefrom, the connector further having a second port adapted for injecting vital life-saving drugs in liquid form into the passageway and then into the distal end of the tube intermixed with the gas, the second port having a portion integrally formed with the connector and a portion separable therefrom, the main axial passageway adapted for atomizing and intermixing of the flow of life-saving drugs with the life-supporting gas.

It is a further object of the invention to provide hospitals and providers of pre-hospital medicine an endotracheal respiration system which allows injection of life-saving drugs into the victim's lungs without interrupting the delivery of oxygen via the ventilation apparatus.

It is a further object of the present invention to fabricate an endotracheal respiration system of relatively few parts and of low cost materials which are easily fabricated, assembled, tested, and packaged in an individual sterile container for use in a use-once, throw-away setting.

It is a further object of the present invention to administer drugs through an endotracheal respiration system in life-threatening emergency settings such as VALIUM for seizures, atropine for organo phosphate poisoning and/or bradyarrhythmias, epinephrine 1:10,000 for cardiac arrest, adreline 1:1,000 for anaphylaxis, lidocaine for arrhythmias, narcan for narcotic overdose, etc.

It is a further object of the present invention to atomize medicinal fluids in a flow of gas for delivery to a patient's lungs.

It is a further object of the invention to configure systems for the introduction of life-supporting fluids so as to introduce the fluids with hypodermic needles and/or syringes as a function of the situation.

Finally, a still further object of the present invention is that the endotracheal respiration system not be limited to only one mode of delivery, e.g., the choice of the life-saving drug should not be limited by the present apparatus.

The foregoing has outlined some of the more pertinent objects of the invention. These objects should be construed to be merely illustrative of some of the more prominent features and applications of the intended invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with the specific embodiment shown in the attached drawings. For the purpose of summarizing the invention, the invention may be incorporated into an improved drug administering endotracheal respiration system for administering vital life-saving drugs into the lungs of a victim while maintaining the flow of life-supporting gas thereto via ventilation apparatus comprising in combination a gas supply; a tube for establishing gas flow exchange between the lungs of the victim and the gas supply, the tube having a proximal end and a distal end for insertion into the trachea of the victim; and a connector for coupling the proximal end of the tube to the gas supply, the connector being formed as a cylinder with a gas input end and a gas discharge end and a linear axial passageway therebetween, the connector having a first port adapted for injecting vital life-saving drugs in liquid form into the passageway and then into the distal end of the tube intermixed with the gas, the first port having a portion integrally formed with the connector and a portion separable therefrom, the connector further having a second port adapted for injecting vital life-saving drugs in liquid form into the passageway and then into the distal end of the tube intermixed with the gas, the second port having a portion integrally formed with the connector and a portion separable therefrom, the main axial passageway adapted for atomizing and intermixing of the flow of life-saving drugs with the life-supporting gas.

The ports are each formed of an interior part molded integrally with the connector and an exterior part threadedly coupled with respect thereto. The ports have axes which are co-planar with respect to the axis of the connector. The connector is adapted to receive the ports at angles substantially 45 degrees with respect to its longitudinal axis or at substantially right angles with respect to its longitudinal axis. The diameter of the passageway is from about three (3) to four (4) times the diameter of each port. At least one of the ports is a hypodermic needle port with a one way rubber member through which a needle is advanced and retracted. At least one of the ports is a syringe port with a one way spring loaded resealable valve opened and closed by the insertion and removal of a syringe. The drug administering endotracheal respiration system further includes a conical step-down area between a larger input end and smaller output end of the connector for increasing the pressure within the connector for the promotion of the intermixing and the lung inflation at which time drug administration takes place.

The invention may also be incorporated into an improved connector between a gas supply and an endotracheal tube, for use in a drug administering respiration endotracheal system for administering vital life-saving drugs into the lungs of the victim while maintaining the life-supporting gas thereto, the connector being formed as a cylinder with a gas input end and a gas discharge end and a linear axial passageway therebetween, the connector having a first port adapted for injecting vital life-saving drugs in liquid form into the passageway and then into the distal end of the tube intermixed with the gas, the first port having a portion integrally formed with the connector and a portion threadedly separable therefrom, the connector further having a second port adapted for injecting vital life-saving drugs in liquid form into the passageway and then into the distal end of the tube intermixed with the gas, the second port having a portion integrally formed with the connector and a portion threadedly separable therefrom, the main axial passageway adapted for atomizing and intermixing of the flow of life-saving drugs with the life-supporting gas.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the disclosed specific embodiments may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in conjunction with the accompanying drawings in which:

FIG. 2 is an elevational view of the connector of FIG. 1 and also showing the related parts of the invention in systems configuration.

FIG. 3 is a sectional view of the connector of FIGS. 1 and 2 taken along the axis thereof.

FIG. 5 is an elevational view of the alternative embodiment of FIG. 4 and also showing the related parts in system configuration.

FIGS. 5A and 5B are enlarged illustrations of the ends of the ports.

Similar reference characters refer to similar parts throughout the several figures.

DETAILED DESCRIPTION OF THE INVENTION

Figure 1:
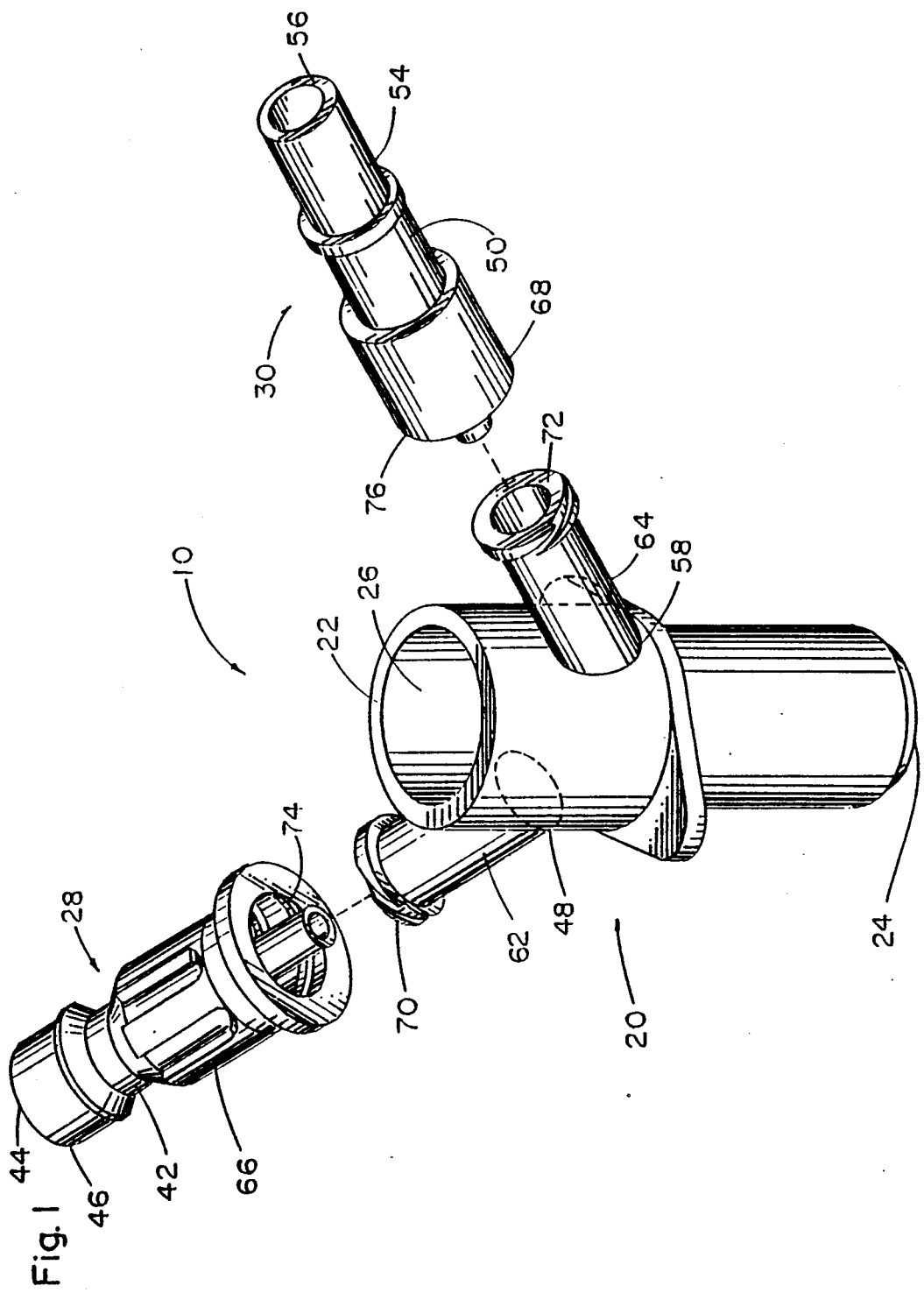
FIG. 1 is a perspective illustration of a connector for a drug administering endotracheal respiration system showing the medication injection ports constructed in accordance with the preferred embodiment of the invention.

With reference to FIGS. 1, 2 and 3, there is shown a drug administering endotracheal respiration system 10 constructed in accordance with the principles of the present invention. A tube 12 supplies life-supporting gasses such as oxygen, air or the like and, if needed, drugs to the lungs of a victim in a life threatening emergency situation. The tube has a distal end 14 for insertion into the trachea of the patient or victim. The proximal end 16 is coupled to a connector 20. A cuff, not shown, located adjacent to the distal end, is inflated after insertion by any conventional means. Although not shown, the inflatable cuff is similar to that disclosed in U.S. Pat. No. 4,600,402 issued to Rosenberg on Jul. 15, 1986 or U.S. Pat. No. 4,700,700 issued to Eliachar on Oct. 20, 1987, which patents are hereby incorporated by reference into this application. The inflation of the cuff urges the tube into sealing engagement with the inner walls of the trachea, thereby establishing gas flow communication between the lungs and the life-supporting gas supply.

The connector 20 has a gas input end 22, a gas discharge end 24, a linear axial passageway 26 therebetween, and a plurality of side ports 28 and 30. The ports extend through apertures 34 and 36 in the wall 38 of the connector 20. The connectors of the disclosed embodiments each illustrate two side ports for each connector, a hypodermic needle port 28 and a syringe port 30. It can be seen that the present invention has the critical advantage of allowing the administration of life-saving drugs without interrupting the flow of life-supporting gasses. In an emergency situation, this critical advantage could be the difference between the victim arriving at the hospital alive or dead.

The hypodermic needle port 28 includes a rigid central tube 42 equipped with a self-sealing rubber membrane 44 at its exterior end 46 that allows penetration by a hypodermic needle for injecting drugs. The membrane re-seals itself completely after withdrawal of the needle to eliminate leakage. This arrangement also precludes the port from becoming a potential source of bacterial infection. The interior end 48 terminates at the passageway 26. Such ports are commercially available as from Abbot Hospital, Inc. as their Model One/No. 5877 entitled Hep Lock.

The syringe port 30 includes a rigid central tube 50 equipped with a one-way, spring-loaded, self sealing valve 54 at its exterior end that allows injection of a life-saving drug. It also re-seals itself after the syringe is withdrawn from the exterior end 56 to eliminate the problem of leakage. This arrangement also precludes the port from becoming a potential source of bacterial infection. The interior end 58 also terminates at the passageway 26. Such ports are commercially available as from intertech/Ohio, Inc. of Fort Myers, Fla. where it is utilized on endotracheal tubes for inflating balloon cuff ports.

Both ports 28 and 30 are one-way, self-sealing ports to promote intermixing of the fluid medicines with the oxygen or other gasses. The needle port is one way via the rubber port through which the needle is advanced and retracted. The syringe port is one way via the spring loaded resealable valve triggered by the inserton and removal of the syringe.

The inner diameter of the gas input end of the connector is about 12.5 millimeters while the output end is about 6.5 millimeters. Intermediate the ends, the linear axial passageway tapers inwardly to form a step down 60. The needle and syringe ports are formed in the side walls of the connector upstream from the step down and adjacent to the input end and have inner diameters of about two (2) to three (3) millimeters. As such, the area of the passageway is from about three (3) to four (4) times larger than the area of each port at its interior end to ensure sufficient gas flow for atomizing the administered liquid drug. The step down of the interior of the connector increases the pressure therein to promote mixing at the higher pressures and also promotes the inflation of the lungs. Such arrangement also reduces to essentially zero the possibility of air embolisms caused by other devices. Such axes are coplanar with the axis of the passageway 26. The general arrangement of parts establishes fixed positions for both ports for greater accessibility by the user as compared with lengthy tubing of prior devices.

As can be seen in the drawings, both ports are formed with two portions, a radially interior section or segment 62 and 64 and a radially exterior section or segment 66 and 68. For each port, the radially interior segment is formed of a tubular member molded integrally with the connector at its associated side opening. Its exterior sections 66 and 68 are engageable with male threads 70 and 72 for receiving the radially exterior segment of the port. The radially interior end of each exterior port segment is formed with internal female threads 74 and 76 adapted to be received on the male threads of the internal portion of the port. The external portion of each port has the mechanisms for allowing the introduction of fluids, generally liquids, either by the syringe or hypodermic needle. The syringe port has a spring and seat arrangement effecting the closure of the passageway through the port until the syringe is inserted therein. The hypodermic needle port has the membrane for allowing closure of the axial passageway until the insertion of the hypodermic needle. Both ports self seal upon the removal of the mechanism, whether hypodermic needle or syringe, and each is adapted to provide the medicinal fluids. In this manner, both ports are self sealing.

This arrangement allows for either port to receive an appropriate external port segment for the particular application. More specifically, each connector can be provided with two syringe ports, two hypodermic needle ports, or one of each.

In operation and use, the paramedic or other health-care provider inserts a tube 12 into the trachea of the emergency victim. Thereupon the cuff is inflated to insure gas flow communication between the victim's lungs and the life-supporting gas supply 80 through connector 20. The connector 120 thus couples the gas supply 80 to the distal end 14. The paramedic, or other health-care provider then establishes a flow of gas, normally air or oxygen, from the source to the victim.

The health-care provider then administers a life-saving drug via the hypodermic needle port 28 or syringe port 30 or both. The positive pressure in the main passageway 26 of the connector 20, supplied by the life-supporting gas supply 80, facilitates atomization or dispersion of the life-saving drug in liquid form into the flow of life-supporting gas and delivery of the medication concurrently with the gas to the lungs of the victim through the process of respiration. The health-care provider is not restricted in the selection of the life-saving drug to only one mode of delivery. The health-care provider can choose a drug in either syringe form or hypodermic form or both. This is effected by selecting and coupling appropriate exterior ends for the ports to accommodate either a syringe and/or hypodermic needle as a function of the situation. Most importantly, however, the administration of the life-saving drug can take place without interrupting the flow of life-supporting gasses.

The design of the present invention features a straight line flow of gas from the source of gas supply 80 to and through the connector 20, to and through the tube 12, to the victim. This design effects a rapid and direct flow of fluid, gas and medication to the victim. The medicines entering the flow of gas are at about a forty five (45) degree angle with respect to the axis of the connector and gas flow for effecting turbulence and intermixing of the medicine and the gas in a rapid and efficient manner. The flow of gas also functions to create a Bernoylli effect with suction to withdraw the medicines from the ports for maximum usage of the available medicine. The distal or interior ends 48 and 58 of the ports are flush with the walls of the passageway 26 to create turbulence which promotes the intermixing of the gas and medicine. The ports being spaced at about the midpoint of the passageway 26 extend the zone for intermixing. The ports are on opposite sides of the connector 20, spaced circumferentially one-hundred eighty (180) degrees for ease of use, separation of hypodermic needle and syringe, and for the promotion of turbulence. This is all for greater efficiency of the system.

Figure 6:
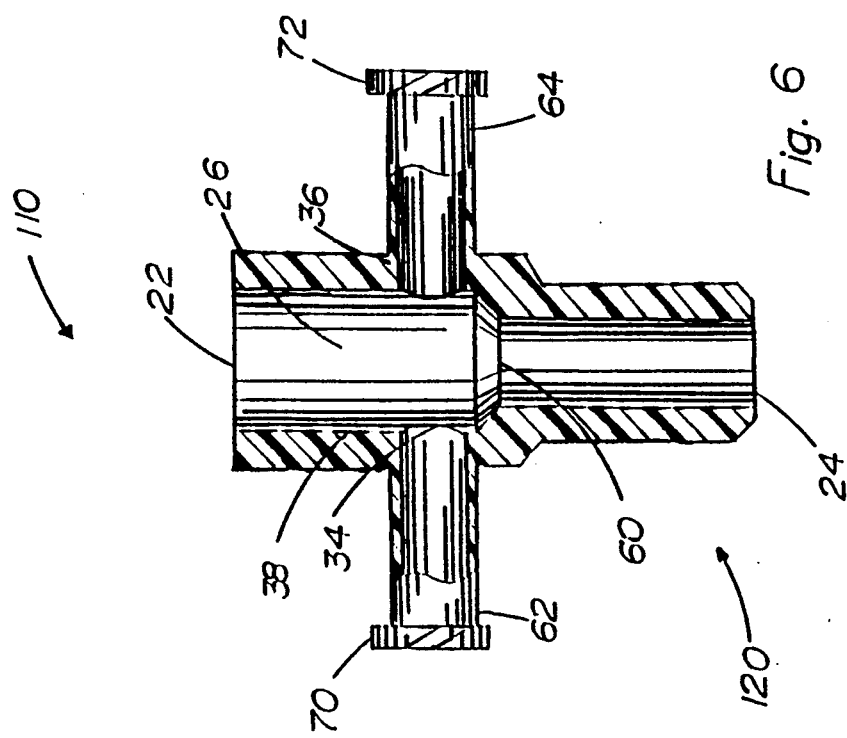
FIG. 6 is a sectional view of the connector of FIGS. 4 and 5 taken along the axis thereof.
Figure 4:
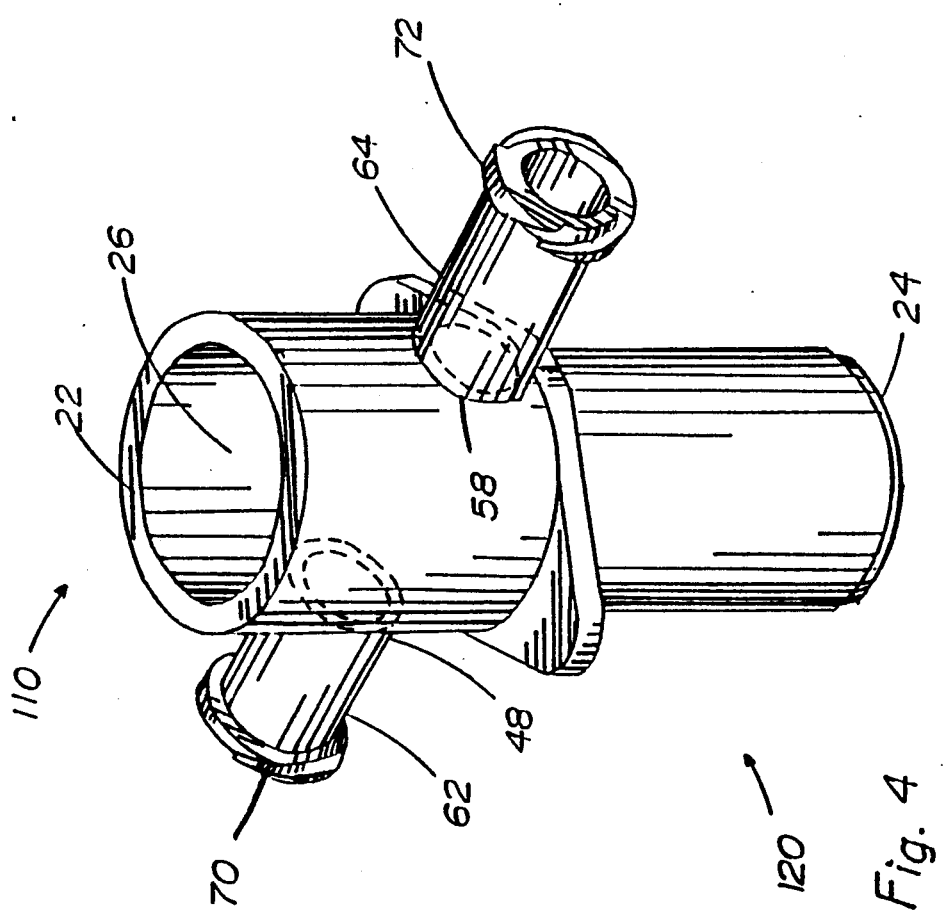
FIG. 4 is a perspective illustration of a connector constructed in accordance with an alternative embodiment of the invention showing the medication injection ports at a ninety (90) degree angle with respect to the linear axial passageway rather than the forty-five (45) degree angle of the primary embodiment.

A second embodiment of the present invention is shown in FIGS. 4, 5 and 6. In the second embodiment, the hypodermic needle port 128 is installed at a ninety degree angle with respect to the connector 120, rather than at forty five (45) degrees of the embodiment of FIGS. 1, 2 and 3. The syringe port 130 is also connected to the connector 120 at a ninety (90) degree angle. All other features of this embodiment are the same as in the prior embodiment.

It has been found that the forty five (45) degree embodiment minimizes the potential spraying of a life-saving drug from one injection port across the diameter of connector to the opposite injection port. The forty-five (45) degree embodiment also accelerates the injection of the life-saving drugs into the life-supporting gas stream and into the patient's lungs more rapidly due to the forty-five (45) degree angle in the direction of the patient's lungs.

Marketing of the present invention may be done by selling either a connector or a system. When selling a connector, commercial deadenders may be screwed over connector ports until used so as to reduce cost.

The present invention, whether the first or second embodiment, in addition to the benefit of selectability of input techniques, has the benefit of the connector being molded of a one piece construction. This reduces cost and precludes the separation of parts which might occur in a design of a multi-piece construction. It also holds the side ports rigid with respect to the axial passageway. Further, the passageways through the connector, through the central longitudinal axis as well as through the side ports, are smooth and continuous with no edges or recesses with sharp or acute angles where injected fluids might become entrapped and dried thus creating a problem with respect to cleanliness. As such, the present invention is safer, more effective and convenient, and less costly than prior designs.

The present disclosure includes that contained in the appended claims as well as that of the foregoing description. Although this invention has been described in its preferred forms with a certain degree of particularity, it is understood that the present disclosure of the preferred form has been made only by way of example and numerous changes in the details of construction and combination and arrangement of parts may be resorted to without departing from the spirit and scope of the invention.

Now that the invention has been described;
What is claimed is:
1. A drug administering endotracheal respiration system for administering vital life-saving drugs into the lungs of a victim while maintaining the flow of life-supporting gas thereto via ventilation apparatus comprising in combination:
  a gas supply;
  a tube for establishing gas flow exchange between the lungs of the victim and the gas supply, the tube having a proximal end and a distal end for insertion into the trachea of the victim; and
  a connector for coupling the proximal end of the tube to the gas supply, the connector being formed as a cylinder with a gas input end and a gas discharge end and a linear main axial passageway therebetween, the connector having a first port adapted for injecting vital life-saving drugs in liquid form into the passageway and then into the distal end of the tube intermixed with the gas, the first port having a portion integrally formed with the connector and a portion separable therefrom, the connector further having a second port adapted for injecting vital life-saving drugs in liquid form into the passageway and then into the distal end of the tube intermixed with the gas, the second port having a portion integrally formed with the connector and a portion separable therefrom, the main axial passageway adapted for atomizing and intermixing of the flow of life-saving drugs with the life-supporting gas.

2. The drug administering endotracheal system as set forth in claim 1 wherein the ports are each formed of an interior part molded integrally with the connector and an exterior part with radially interior threads engageable with respect to radially exterior threads on the interior part.

3. The drug administering endotracheal respiration system as set forth in claim 1 wherein the ports have axes which are co-planar with respect to the axis of the connector.

4. The drug administering endotracheal respiration system as set forth in claim 1 wherein the connector is adapted to receive the ports at angles substantially 45 degrees with respect to its longitudinal axis.

5. The drug administering endotracheal respiration system as set forth in claim 1 wherein the connector is adapted to receive the ports at substantially right angles with respect to its longitudinal axis.

6. The drug administering endotracheal respiration system as set forth in claim 1 wherein the diameter of the passageway is from about three (3) to four (4) times the diameter of each port.

7. The drug administering endotracheal respiration system as set forth in claim 1 wherein at least one port is a hypodermic needle port with a one way rubber member through which a needle is advanced and retracted.

8. The drug administering endotracheal respiration system as set forth in claim 1 wherein at least one port is a syringe port with a one way, spring loaded, resealable valve opened and closed by the insertion and removal of syringe.

9. The drug administering endotracheal respiration system as set forth in claim 1 and further including a conical step-down area between a larger input end and smaller output end of the connector for increasing the pressure within the connector for the promotion of the intermixing and the lung inflation at which time drug administration takes place.

10. For use in a drug administering respiration endotracheal system for administering vital life-saving drugs into the lungs of the victim while maintaining the life-supporting gas thereto, an improved connector between a gas supply and an endotracheal tube, the connector being formed as a cylinder with a gas input end and a gas discharge end and a linear main axial passageway therebetween, the connector having a first port adapted for injecting vital life-saving drugs in liquid form into the passageway and then into the distal end of the tube intermixed with the gas, the first port having a portion integrally formed with the connector and a portion threadedly separable therefrom, the connector further having a second port adapted for injecting vital life-saving drugs in liquid form into the passageway and then into the distal end of the tube intermixed with the gas, the second port having a portion integrally formed with the connector and a portion threadedly separable therefrom, the main axial passageway adapted for atomizing and intermixing of the flow of life-saving drugs with the life-supporting gas.

* * * * *